United States Patent [19]

Stach

[11] 4,256,741
[45] Mar. 17, 1981

[54] PYRIDYL ESTERS OF N-ALKYLIDENE-SUBSTITUTED PHOSPHOR- AND PHOSPHONAMIDIC ACIDS

[75] Inventor: Leonard J. Stach, Riverside, Ill.

[73] Assignee: Velsicol Chemical Corporation, Chicago, Ill.

[21] Appl. No.: 140,058

[22] Filed: Apr. 14, 1980

Related U.S. Application Data

[62] Division of Ser. No. 46,299, Jun. 7, 1979, Pat. No. 4,226,859.

[51] Int. Cl.³ .................. C07D 213/74; A01N 57/16
[52] U.S. Cl. ...................................... 424/200; 546/25
[58] Field of Search ........................... 546/25; 424/200

[56] References Cited

U.S. PATENT DOCUMENTS

| | | | |
|---|---|---|---|
| 3,669,975 | 6/1972 | Demosay | 546/25 |
| 3,743,648 | 7/1973 | Rigterink | 546/25 |
| 3,911,118 | 10/1975 | O'Melia | 424/200 |
| 4,087,430 | 5/1978 | Pawloski | 546/25 |

Primary Examiner—Alan L. Rotman
Attorney, Agent, or Firm—Dietmar H. Olesch; Robert J. Schwarz

[57] ABSTRACT

This invention discloses chemical compounds of the formula

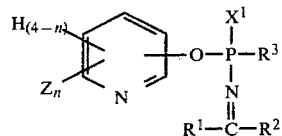

wherein $X^1$ is selected from the group consisting of oxygen and sulfur; $R^1$ is selected from the group consisting of hydrogen, alkyl, phenyl, alkoxy and alkylthio; $R^2$ is selected from the group consisting of alkoxy, alkylthio, amino, alkylamino and dialkylamino; with the proviso that a maximum of one of $R^1$ and $R^2$ is alkoxy or alkylthio; Z is selected from the group consisting of alkyl, alkoxy, nitro and halogen; and n is an integer from 0 to 4; and wherein $R^3$ is selected from the group consisting of alkyl, alkoxy, alkylthio and

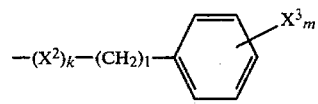

wherein $X^2$ is selected from the group consisting of oxygen and sulfur; $X^3$ is halogen, k is the integer 0 or 1; and l and m are each integers from 0 to 3.

Further disclosed are insecticidal compositions utilizing the compound of the present invention.

10 Claims, No Drawings

PYRIDYL ESTERS OF N-ALKYLIDENE-SUBSTITUTED PHOSPHOR- AND PHOSPHONAMIDIC ACIDS

This is a division of application Ser. No. 46,299 filed June 7, 1979, now U.S. Pat. No. 4,226,859 issued Oct. 7, 1980.

This invention relates to new compositions of matter and more specifically relates to new compounds of the formula

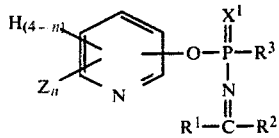

wherein $X^1$ is selected from the group consisting of oxygen and sulfur; $R^1$ is selected from the group consisting of hydrogen, alkyl, phenyl, alkoxy and alkylthio; $R^2$ is selected from the group consisting of alkoxy, alkylthio, amino, alkylamino and dialkylamino; with the proviso that a maximum of one of $R^1$ and $R^2$ is alkoxy or alkylthio; Z is selected from the group consisting of alkyl, alkoxy, nitro and halogen; and n is an integer from 0 to 4: and wherein $R^3$ is selected from the group consisting of alkyl, alkoxy, alkylthio and

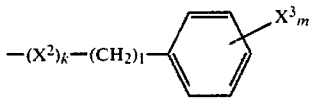

wherein $X^2$ is selected from the group consisting of oxygen and sulfur; $X^3$ is halogen; k is the integer 0 or 1; and l and m are each integers from 0 to 3.

The compounds of the present invention are unexpectedly useful as insecticides.

In a preferred embodiment of this invention, $X^1$ is selected from the group consisting of oxygen and sulfur; $R^1$ is selected from the group consisting of hydrogen, lower alkyl, lower alkoxy, lower alkylthio and phenyl; $R^2$ is selected from the group consisting of lower alkoxy, lower alkylthio, lower alkylamino and lower dialkylamino; with the proviso that a maximum of one of $R^1$ and $R^2$ is lower alkoxy or lower alkylthio; Z is selected from the group consisting of lower alkyl, lower alkoxy, nitro and halogen and n is an integer from 0 to 4; and wherein $R^3$ is selected from the group consisting of lower alkyl, lower alkoxy, lower alkythio and

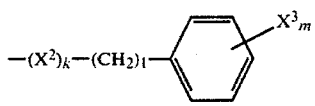

wherein $X^2$ is selected from the group consisting of oxygen and sulfur; $X^3$ is halogen; k is the integer 0 or 1; and l and m are each integers from 0 to 3.

The term "lower" as used herein designates a straight or branched chain of up to 6 carbon atoms.

The compounds of the present invention wherein Z, $X^1$, $R^3$ and n are as heretofore described and $R^2$ is amino, alkylamino or dialkylamino can be prepared by reacting a compound of the formula

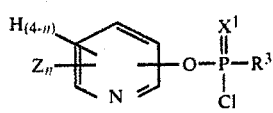

wherein, Z, $X^1$, $R^3$ and n are as heretofore described with a compound of the formula

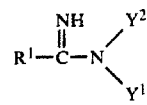

wherein $R^1$ is as hereinbefore described and $Y^1$ and $Y^2$ are, independently, hydrogen or alkyl. $Y^1$ and $Y^2$ in combination with the nitrogen atom adjacent them form the group $R^2$ where $R^2$ is amino, alkylamino or dialkylamino. Typically, the compounds of formula III are used in the form of their salts, such as the hydrochloride or the hydrogen sulfate. This reaction can be effected by combining the compounds of formula II and III in an inert organic reaction medium, such as ether, at a temperature of about 0° to about 40° C., followed by the incremental addition of aqueous inorganic base, such as an alkali metal hydroxide. A slight excess molar amount of the compound of formula III and a large excess of base, such as 2 or 3 molar amounts based on the moles of compound II can be used. After the addition of base is completed, the reaction mixture can be stirred for an additional period of up to about 4 hours to ensure completion of the reaction. After this time the desired product can be recovered from the organic phase upon removal of the solvent. The product can then be used as such or can be further purified by standard techniques known in the art.

The compounds of the present invention wherein $R^2$ is amino, alkylamino or dialkylamino can also be prepared by reacting a compound of formula

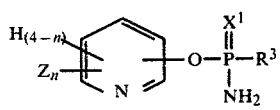

wherein $R^3$, $X^1$, Z and n are as hereinbefore described with an acetal of the formula

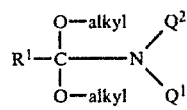

wherein $R^1$ is as hereinbefore described and $Q^1$ and $Q^2$ are independently hydrogen or alkyl. $Q^1$ and $Q^2$ in combination with the nitrogen atom adjacent them form the group $R^2$ where $R^2$ is amino, alkylamino or dialkyl amino. This reaction can be carried out by combining an inert reaction medium such as ether, methylene chloride or chloroform, the compound of formula IV with a slight molar excess of the acetal of formula V at room temperature with stirring. Typically a slight exotherm may be observed. After the exotherm has subsided, the reaction mixture can be heated at a temperature of up to about 80° C. for a period of up to about 2 hours to ensure completion of the reaction. After this time the reaction mixture can be subjected to vacuum to remove unreacted starting material, volatile reaction by-products and solvent thereby yielding the desired product. This product can be used as such or can be further purified by conventional techniques in the art.

The compounds of the present invention wherein $R^3$, $X^1$ and $Z$ and $n$ are as hereinbefore described, $R^1$ is hydrogen, alkyl or phenyl; and $R^2$ is alkoxy or alkylthio may be prepared by reacting a compound of formula IV with a compound of formula

(VI)

wherein $R^1$ is hydrogen, alkyl or phenyl; Y is alkyl and $X^4$ is oxygen or sulfur. The combination of $X^4$ and Y constitutes an alkoxy or an alkylthio embodiment of $R^2$. The reaction is effected by combining compounds IV and VI, refluxing from about 2 to about 4 hours, then removing unreacted starting materials under vacuum leaving the desired product as the residue. This residue can be used as such or further purified by conventional techniques if desired.

When not available, the compounds of formula II may be prepared by reacting a compound of formula

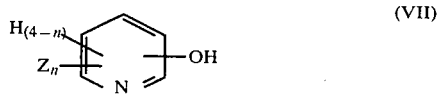
(VII)

wherein Z and n are as hereinbefore described, with a compound of formula

(VIII)

wherein $X^1$ and $R^3$ are as hereinbefore described. This reaction can be effected by combining the compounds of formula VII and VIII in a dry inert organic reaction medium, such as ether or methylene chloride at a temperature of from about 0° to 40° C. and thereafter incrementally adding an equimolar or slightly excess molar amount of an acid acceptor, such as a tertiary amine, with stirring, at a temperature of from about 0° C. to about 40° C. When the addition is completed, stirring can be continued for a period of several hours to ensure completion of the reaction. After this time the reaction mixture can be filtered to remove the acid acceptor chloride that has formed. The remaining reaction mixture can then be stripped of solvent to yield the desired product or can be left in solution while it is further reacted. An alternate method of preparing the compounds of formula II is to dissolve or slurry the compound of formula VII in an inert reaction medium such as methyl isobutyl ketone, add a 50% aqueous solution of sodium hydroxide containing a molar amount of sodium hydroxide equal to, or slightly in excess of, the moles of the formula VII compound, heat to reflux and then strip off the water by azeotropic distillation. To the water-free solution is then added slowly, with stirring, a molar amount of the formula VIII compound equal to, or slightly in excess of, the moles of the formula VII compound. The reaction is carried out at about 0° to 10° C. Stirring may be continued for several hours after the addition to ensure completion reaction. The product may be used in further reaction while still in its reaction solution or may be isolated and purified by conventional means.

The compounds of formula IV can be prepared by reacting a compound of formula II, as hereinbefore described, in an inert organic reaction medium such ether or methylene chloride with dissolved or gaseous $NH_3$ at a temperature of from about $-30°$ C. to about 15° C. A molar excess of $NH_3$ is used and the reaction mixture is stirred for from about 2 hours to about 4 hours at room temperature. The precipitated solid $NH_4Cl$ can then be removed by filtration and washed with the solvent used in the reaction. These washings can be added to the filtered reaction mixture. The product may be left in solution for further reaction or may be isolated and purified by conventional techniques.

Exemplary compounds of formula III useful for preparing the compounds of this invention are 2-propyl-1-ethyl-1-propylisourea; 2-dodecyl-1,dihexylisourea; 2-(3-methylbutyl)-1-ethylisourea; 2-heptyl-1,1-(2-methylpropyl)isourea; 2-ethyl-1-propyl-1-butylisothiourea; 2-nonyl-1,1-(2,3-diethylhexyl)isothiourea; 2-(2,3,4-trimethylpentyl)-1-pentylisothiourea; 2-butyl-1,1-dipropylisothiourea; $N^1,N^1$-dimethylformamidine; $N^1$-methyl-$N^1$-ethyl acetamidine; $N^1,N^1$-diethylbenzamidine; $N^1,N^1$-dibutyl-2-methylpropanamidine; $N^1,N^1$-di(3,3-dimethylbutyl)decanamidine.

Exemplary compounds of formula V useful for preparing the compounds of this invention are N,N-dimethyl-1,1-dimethoxypropylamine; N,N-diethyl-dimethoxymethylamine; N-propyl-(phenyl)(dimethoxy)methylamine;

Exemplary compounds of formula VI useful for preparing the compounds of this invention are tri(2-methylpropyl)orthopentanoate; trimethylorthoformate, triethylorthoacetate; trihexylorthoheptanoate; tributylortho(phenyl)formate; trimethylthiomethane; 1,1,1-triethylthioethane.

Exemplary compounds of formula VII useful for preparing the compounds of this invention are 4-Methyl-3-hydroxypyridine; 3,4-dichloro-2-hydroxpyridine; 3-nitro-4-chloro-2-hydroxypyridine; 3-Methoxy-4-ethyl-5-chloro-2-hydroxypyridine; 2-methyl-3,4-dichloro-2-hydroxypyridine; 3,5-dinitro-5-hydroxypyridine; 4-propoxy-5-chloro-3-hydroxy-pyridine; 3,5-dinitro-5-(2-ethylpropyl)-4-hydroxypyridine.

Exemplary compounds of formula VIII useful for preparing the compounds of this invention are ethylphosphonic dichloride, 2-methylpropylphosphonic dichloride, octylphosphonic dichloride, 2,3-diethylnonylphosphonic dichloride, hexylphosphonothionic dichloride, phenylphosphonic dichloride, phenylphosphonothionic dichloride; O-propyl phosphorodichloridate; O-(2,3-diethylhexyl) phosphorodichloridate; O-dodecyl phosphorodichloridate; O-(2-butylhexyl) phosphorodichloridothionate; O-(3,4-dimethylheptyl) phosphorodichloridothionate; S-butyl phosphordichloridothiolate; S-nonyl phosphorodichloridothiolate; S-(2-methylpropyl) phosphorodichloridothiolothionate, S-decyl phosphorodichloridothiolothionate; O-phenylmethyl phosphoroddichloridothionate, O-(3,5-dichloro-2-ethylphenyl) phosphorodichloridothionate, S-(2,4,6-trifluoro-3-propylphenyl) phosphorodichloridothiolate.

The manner in which the compounds of this present invention can be prepared is more specifically illustrated in the following examples.

EXAMPLE 1

Preparation of O-(3,5,6-trichloro-2-pyridyl) O-ethyl Phosphorochloridothionate 3,5,6-Trichloro-2-hydroxypyridine (9.15 grams; 0.05 mole) was dissolved in 100 ml benzene and filtered through diatomaceous earth. The filtrate and triethylamine (5.05 grams; 0.05 mole) were charged into a glass reaction vessel fitted with a mechanical stirrer and thermometer and cooled to about 5° C. To this mixture was added dropwise with stirring over 10 minutes a solution of O-ethyl phosphorodichloridothionate in 100 ml of benzene while holding the reaction temperature no higher than about 5° C. The mixture was stirred at about 5° C. for 0.5 hour, then warmed to 60° C. and stirred an additional 0.25 hour. The mixture was filtered and the filtrate washed with benzene. The washings were combined with the filtrate which contained the desired product O-(3,5,6-trichloro-2-pyridyl) O-ethyl phosphorochloridothionate which was left in solution for further reaction.

EXAMPLE 2

Preparation of O-(3,5,6-trichloro-2-pyridyl) O-ethyl Phosphoramidothionate

O-(3,5,6-Trichloro-2-pyridyl) O-ethyl phosphorochloridothionate (16 grams; 0.05 mole) in the solution of example 1 was added dropwise over 0.5 hour to ammonia (3 grams; 0.18 mole) in 50 ml diethyl ether. Addition was started at −50° C. and the reaction temperature held to −15° C. maximum. Stirring was continued for 0.5 hour at about −10° C. The mixture was allowed to warm to 0° C. and then filtered. The filtrate was washed twice with 30 ml portions of water then dried with phase separation paper. The solent was stripped off by mild warming under reduced pressure to yield the desired product O-(3,5,6-trichloro-2-pyridyl) O-ethyl phosphoroamidothionate.

EXAMPLE 3

Preparation of O-(3,5,6-trichloro-2-pyridyl) O-ethyl N-(dimethylaminomethylene) Phosphoramidothionate

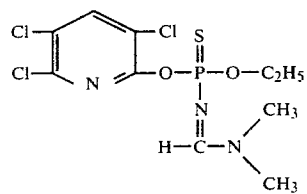

O-(3,5,6-Trichloro-2-pyridyl) O-ethyl phosphoramidothionate (2.25 grams; 0.007 mole) was dissolved in 40 ml of benzene and the solution charged into a glass reaction vessel fitted with a mechanical stirrer and thermometer. N,N-Dimethylformamide dimethyl acetal (2.0 grams; 0.017 mole) was added at room temperature (slight exotherm noted). The reaction mixture was stirred at room temperature for about 20 hours. The solvent was removed by mild warming under reduced pressure to give a yellow brown oil which was crystallized from diisopropyl ether to yield the desired product O-(3,5,6-trichloro-2-pyridyl) O-ethyl N-(dimethylaminomethylene) phosphoramidothionate, as a white solid having a melting point of 93° to 96° C.

EXAMPLE 4

Preparation of O-(3,5,6-trichloro-2-pyridyl) Ethylphosphonochloridothionate 3,5,6-Trichloro-2-hydroxypyridine (9.15 grams; 0.05 mole) and 100 ml of benzene were charged into a glass reaction vessel fitted with a mechanical stirrer and thermometer and the mixture cooled to about 10° C. Triethylamine (5.05 grams; 0.05 mole) was added. The resulting mixture was cooled to 50° C. and ethylphosphonothionic dichloride (8.19 grams; 0.05 mole) dissolved in 10 ml of benzene was added dropwise, with stirring, at this temperature. Stirring was continued for 1 hour at 50° C. The mixture was allowed to warm to room temperature, held an additional 0.5 hour at room temperature, then filtered. The filtered-off solids were washed with benzene and the washings combined with filtrate. The desired product O-(3,5,6-trichloro-2-pyridyl) ethylphosphonochloridothionate was not isolated but was left in solution for further reaction.

EXAMPLE 5

Preparation of O-(3,5,6-trichloro-2-pyridyl) Ethylphosphonamidothionate

Ammonia (2.5 grams; 0.15 mole) was dissolved in 50 ml of diethyl ether cooled to −30° C. and contained in a glass reaction vessel fitted with a mechanical stirrer and thermometer. O-(3,5,6-Trichloro-2-pyridyl) ethylphosphonochloridothionate contained in the solution of example 5 (0.05 mole) was added dropwise, with stirring, over 45 minutes, to the ammonia solution while holding the temperature at about −30° C. The reaction mixture was stirred 0.25 hours at −10° C. It was then let warm to room temperature and filtered. The filtered-off solids were washed with 10 ml benzene and the washings combined with the filtrate which contained the desired product O-(3,5,6-trichloro-2-pyridyl) ethylphosphonamidothionate which was left in solution for further reaction.

EXAMPLE 6

Preparation of O-(3,5,6-trichloro-2-pyridyl) N-(dimethylaminomethylene) Ethylphosphonamidothionate

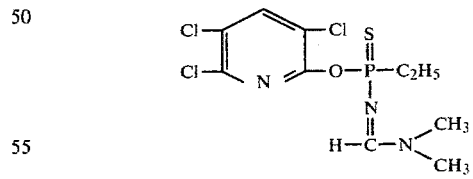

O-(3,5,6-Trichloro-2-pyridyl) ethylphosphonamidothionate (0.025 mole) in the solution of example 5 was charged into a glass reaction vessel fitted with a mechanical stirrer and thermometer. N,N-Dimethylformamide dimethyl acetal (4.0 grams; 0.033 mole) was added and the resulting mixture stirred 16 hours at room temperature. The solvent was removed under mild heat and reduced pressure to yield a yellow oil which crystallized to a wet solid. This solid was recrystallized from diethyl ether and then from diisopropyl ether to yield the desired product O-(3,5,6-trichloro-2- pyridyl) N-(dimethylaminomethylene)ethylphosphonamidothionate as a white solid having a melting point of 77° to 79° C.

EXAMPLE 7

Preparation of O-(2-chloro-3-pyridyl) O-ethyl Phosphorochloridothionate

2-Chloro-3-hydroxy pyridine (10 grams; 0.08 mole) and 50 ml of diethyl ether were charged into a glass reaction vessel fitted with a mechanical stirrer and thermometer. The mixture was cooled to 0° C. and ethyl phosphorodichloridothionate (20.7 grams; 0.12 mole) was added dropwise while keeping temperature at about 0° C. Triethylamine (12.1 grams; 0.12 mole) was then added dropwise while keeping the temperature at about 0° C. Stirring was continued for 2 hours at room temperature. The reaction mixture was filtered to remove triethylamine hydrochloride and the solvent stripped off under reduced pressure to yield the desired product O-(2-chloro-3-pyridyl) O-ethyl phosphorochloridothionate.

EXAMPLE 8

Preparation of O-(2-chloro-3-pyridyl) O-ethyl Phosphoramidothionate

O-(2-Chloro-3-pyridyl) O-ethyl phosphorochloridothionate (28 grams; 0.11 mole) and 200 ml of diethyl ether were charged to a glass reaction vessel fitted with a mechanical stirrer and thermometer. The solution was cooled to 0° C. and NH₃ (0.2 mole) was bubbled through it while holding the temperature at about 0° C. and stirring vigorously. After the addition was finished, the reaction mixture was stirred 2 hours at room temperature. The precipitated NH₄Cl was filtered off and washed with ether. The washings were combined with the filtrate and the ether stripped off under reduced pressure to give the product O-(2-chloro-3-pyridyl) O-ethyl phosphoramidothionate.

EXAMPLE 9

Preparation of O-(2-chloro-3-pyridyl) O-ethyl N-(methoxymethylene) Phosphoramidothionate

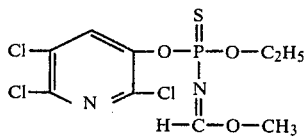

O-(2-Chloro-3-pyridyl) O-ethyl phosphoramidothionate (5.2 grams; 0.021 mole) was charged to a glass reaction vessel fitted with a mechanical stirrer and thermometer. Trimethyl orthoformate (10 ml) was added and the reaction mixture refluxed for 2 hours. The byproduct methanol and unreacted orthoformate was removed under reduced pressure. The residue was dissolved in diethyl ether and filtered through diatomaceous earth. The solvent was then removed under reduced pressure to yield the desired product O-(2-chloro-3-pyridyl) O-ethyl N-(methoxymethylene)phosphoramidothionate as a dark red liquid.

EXAMPLE 10

Preparation of O-(2-chloro-3-pyridyl) O-ethyl N-(1-ethoxyethylidene) Phosphoramidothionate

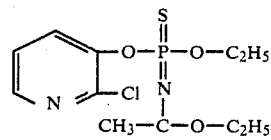

O-(2-Chloro-3-pyridyl) O-ethyl phosphoramidothionate (4.0 grams; 0.016 mole) was charged to a glass reaction vessel fitted with a mechanical stirrer and thermometer. Triethyl orthoacetate (10 ml) was added and the mixture heated at 80° C. for 2 hours. The mixture was then cooled and stirrer overnight at room temperature. Ethanol and unreacted orthoacetate were removed under reduced pressure. The residue was dissolved in diethyl ether and the solution filtered through diatomaceous earth. The solvent was removed under reduced pressure to yield the desired product O-(2-chloro-3-pyridyl) O-ethyl N-(1-ethoxyethylidene) phosphoramidothionate as a red brown oil.

EXAMPLE 11

Preparation of O-(2-chloro-3-pyridyl) O-ethyl N-(dimethylaminomethylene) Phosphoramidothionate

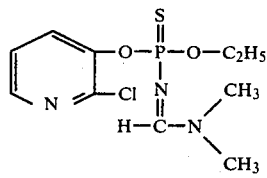

O-(2-chloro-3-pyridyl) O-ethyl phosphoramidothionate (6.0 grams; 0.024 mole), was charged to a glass reaction vessel fitted with a mechanical stirrer and thermometer. 10 ml of N,N-dimethylformamide dimethyl acetal was added and the reaction mixture stirred 16 hours at room temperature. Byproduct methanol and unreacted DMF acetal was removed under reduced pressure to yield the desired product O-(2-chloro-3-pyridyl) O-ethyl N-(dimethylaminomethylene)phosphoramidothionate as a dark red oil.

EXAMPLE 12

Preparation of O-(6-methyl-3-pyridyl) O-ethyl Phosphorochloridothionate

6-Methyl-3-hydroxypyridine (98.4 grams; 0.9 mole) and 1800 ml of methyl isobutyl ketone were charged into a glass reaction vessel fitted with a mechanical stirrer, thermometer and Dean Stark trap. A 50% (wt.) aqueous solution of sodium hydroxide (72 grams of 50% solution; 0.9 mole NaOH) was added with stirring. The reaction mixture was heated to reflux and the water stripped off by azeotropic distillation. The reaction mixture was cooled to 5° C. and 120 ml (0.9 mole) of ethyl phosphordichloridothionate was added dropwise, with stirring while holding temperature at about 10° C. The reaction mixture was stirred for two hours at room temperature after ending the addition. The product O-(6-methyl-3-pyridyl) O-ethyl phosphorochloridothionate was left in solution for further reaction.

EXAMPLE 13

Preparation of O-(6-methyl-3-pyridyl) O-ethyl Phosphoramidothionate

The solution of example 12 containing O-(6-methyl-3-pyridyl) O-ethyl phosphorochloridothionate was cooled to 5° C. and ammonia gas bubbled through it for 2 hours. Stirring was continued at room temperature for 0.5 hours after the conclusion of the NH3 addition. The reaction mixture was let stand 48 hours was then filtered. The filtered-off solids were washed with methyl isobutyl ketone and the washings combined with the filtrate. The filtrate was washed with two 600 ml portions of water, three 300 ml portions of 0.1 N aqueous sodium hydroxide, and one 600 ml portion of water. The filtrate was then dried and the solvent removed under reduced pressure to give a red-orange oil. A solid precipitated. The solids and the oil were extracted with diethyl ether, the ether solution decanted off and water washed and dried. The ether was removed under reduced pressure to yield a thick red oil. Solids precipitated again. The treatment with diethyl ether and water washing was repeated. On stripping off the ether under reduced pressure, the product O-(6-methyl-3-pyridyl) O-ethyl phosphoramidothionate was obtained as a thick oil.

EXAMPLE 14

Preparation of O-(6-methyl-3-pyridyl) O-ethyl N-(1-ethoxyethylidene) Phosphoramidothionate

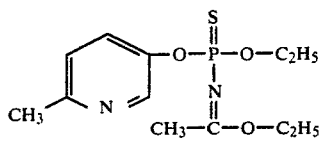

O-(6-Methyl-3-pyridyl) O-ethyl phosphoramidothionate (3.5 grams; 0.015 mole), and 25 ml of methylene chloride were charged into a glass reaction vessel fitted with a mechanical stirrer and thermometer. Triethyl orthoacetate, 3 ml, (2.68 grams; 0.017 mole) was added and the mixture was stirred overnight at room temperature. Apparently little reaction occured. The reaction mixture was then refluxed for one hour and the solvent stripped off under reduced pressure. An additional 10 ml of triethyl orthoacetate was added and the mixture heated to 100° C. for 2 hours. Reaction was found to take place. The solvent was removed under reduced pressure and the residue further held under high vacuum to yield the desired product O-(6-methyl-3-pyridyl) O-ethyl N-(1-ethoxyethylidene)phosphoramidothionate as a dark orange liquid.

EXAMPLE 15

Preparation of O-(6-methyl-3-pyridyl) O-ethyl N-(methoxymethylene) Phosphoramidothionate

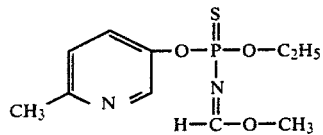

O-(6-Methyl-3-pyridyl) O-ethyl phosphoramidothionate (4.6 grams; 0.02 mole) and 10 ml of trimethyl orthoformate were charged to a glass reaction vessel fitted with a mechanical stirrer and thermometer and refluxed for 4 hours. The reaction mixture was then cooled and the unreacted trimethyl orthoformate and methanol removed under reduced pressure. The residue was washed three times with 100 ml portions of diethyl ether. These ether washings were combined and filtered through Celite. The ether was stripped off under reduced pressure to yield the desired product O-(6-methyl-3-pyridyl) O-ethyl N-(methoxymethylene) phosphoramidothionate as a dark orange liquid.

EXAMPLE 16

Preparation of O-(6-methyl-3-pyridyl) O-ethyl N-(dimethylaminomethylene) Phosphoramidothionate

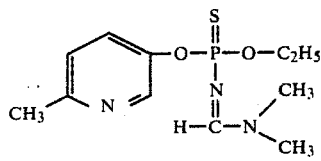

O-(6-Methyl-3-pyridyl) O-ethyl phosphoramidothionate (104 grams; 0.448 mole) and 200 ml of methylene chloride were charged into a glass reaction vessel fitted with a mechanical stirrer and thermometer and the mixture stirred until completed solution occured. N,N-Dimethylformamide dimethyl acetal (53.4 grams; 0.448 mole) was added and the mixture stirred 16 hours at room temperature. Methylene chloride, methanol and unreacted DMF-acetal were then stripped off under reduced pressure; the residue, a brown oil, was held under high vacuum for 2 hours. This residue was chromatographed on a prep-scale liquid chromatography silica gel column using a 17:3 methylene chloride:acetone solvent. The fraction containing the product was selected and the solvent was stripped off under reduced pressure. The residue was washed with hexane to remove hexane-soluble contaminants. Volatiles were then stripped off under reduced pressure and the residue held under high vacuum for 4 hours to yield the desired product O-(6-methyl-3-pyridyl) O-ethyl N-(dimethylaminomethylene)phosphoramidothionate as a thick dark orange oil.

EXAMPLE 17

Preparation of O-(3-pyridyl) O-ethyl Phosphorochloridothionate

3-Hydroxy pyridine (9.5 grams; 0.1 mole) and 200 ml of diethyl ether were charged into a glass reaction vessel fitted with a mechanical stirrer and thermometer. The mixture was cooled to 0° C. and ethyl phosphorodichloridothionate (20.7 grams; 0.12 mole) was added dropwise with stirring while holding the temperature about 0° C. To the reaction mixture was then added dropwise, with stirring, triethylamine (12.1 grams; 0.12 mole) while keeping the temperature at about 0° C. Stirring was continued for 2 hours after the amine addition while keeping the maximum temperature at about 20° C. The product O-(3-pyridyl) O-ethyl phosphorochloridothionate was left in solution for further reaction.

EXAMPLE 18

Preparation of O-(3-pyridyl)O-ethyl Phosphoramidothionate

The solution of O-(3-pyridyl) O-ethyl phosphorochloridothionate prepared in example 17 was filtered and charged into a glass reaction vessel fitted with a mechanical stirrer and thermometer. Ammonia (5 grams; 0.3 mole) was bubbled through the solution at room temperature. Stirring was continued at room temperature for 1.5 hours after the ammonia addition. The reaction mixture was then filtered and the filtered-off solids washed with diethyl ether. These washings were combined with the filtrate and solvent was stripped off under reduced pressure. The residue was redissolved in diethyl ether and the solution filtered through diatomaceous earth. The ether was removed under reduced pressure, the residue was redissolved in diethyl ether and this solution washed twice with water, once with 0.5 N aqueous sodium hydroxide and twice more with water. The solution was then dried and the solvent removed under reduced pressure. The residue was dissolved in methylene chloride and cromatographed on a column of fullers earth. Fractions containing the product, identified by thin layer chromatography and infra red, were isolated and combined. Solvent was stripped off under reduced pressure to yield the desired product O-(3-pyridyl) O-ethyl phosphoramidothionate.

EXAMPLE 19

Preparation of O-(3-pyridyl) O-ethyl N-(dimethylaminomethylene) Phosphoramidothionate

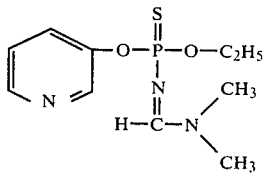

O-(3-Pyridyl) O-ethyl phosphoramidothionate (2 grams; 0.00917 mole) and 30 ml of methylene chloride were charged to a glass reaction vessel fitted with a mechanical stirrer and thermometer. To this mixture was added N,N-dimethylformamide dimethyl acetal (1.31 grams; 0.011 mole). The mixture was stirred 16 hours at room temperature. The solvent, methanol and unreacted N,N-dimethylformamide dimethyl acetal were stripped off under reduced pressure. The residue was then held under high vacuum for 1 hour to yield the desired product O-(3-pyridyl) O-ethyl N-(dimethylaminomethylene) phosphoramidothionate as a dark red liquid.

EXAMPLE 20

Preparation of O-(3-pyridyl) Ethylphosphonochloridothionate

3-Hydroxypyridine (19.0 grams; 0.2 mole), 100 ml of ether and triethylamine (20.2 grams; 0.2 mole) were charged into a glass reaction vessel fitted with a mechanical stirrer and thermometer and cooled to 0° C. Ethylphosphonothionic dichloride (32.6 grams; 0.2 mole) dissolved in 100 ml of ether was then added dropwise in 1 hour while holding the temperature at about 0° C. The reaction mixture was then stirred 1 hour at room temperature, the precipitated triethylamine hydrochloride was filtered off and the precipitate washed with ether. These washings were combined with the filtrate. The product O-(3-pyridyl) ethylphosphonochloridothionate was left in solution to be further reacted.

EXAMPLE 21

Preparation of O-(3-Pyridyl) Ethylphosphonamidothionate

The solution of O-(3-pyridyl) ethylphosphonochloridothionate of example 20 was charged into a glass reaction vessel fitted with a mechanical stirrer and thermometer and containing a solution of ammonia (0.2 mole) dissolved in diethyl ether and cooled to a temperature of about −30° C. Temperature was held at about −30° C. during the addition. The reaction mixture was then stirred 16 hours at room temperature and then filtered to remove solid ammonium chloride. The desired product O-(3-pyridyl) ethylphosphonamidothionate was left in solution for further reaction.

EXAMPLE 22

Preparation of O-(3-pyridyl) N-(dimethylaminomethylene)ethylphosphonamidothionate

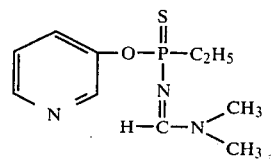

The solution of O-(3-pyridyl) ethylphosphonamidothionate prepared in example 21 was charged into a glass reaction vessel fitted with a mechanical stirrer and thermometer. N,N-Dimethyl formamide dimethyl acetal (23.8 grams; 0.2 mole) dissolved in 50 ml of diethyl ether was added at room temperature and the reaction mixture stirred for 16 hours at room temperature. The solvent was then stripped off under reduced pressure to yield the desired product O-(3-pyridyl) N-(dimethylaminomethylene)ethylphosphonamidothionate

EXAMPLE 23

Preparation of O-(2-pyridyl) O-ethyl Phosphorochloridothionate

2-Hydroxypyridine (19.02 grams; 0.2 moles) was charged into a glass reaction vessel fitted with a mechanical stirrer and thermometer. Diethyl ether 400 ml, was added, the mixture cooled to 0° C. and ethyl phosphorodichloridothionate (30.6 ml; 41.5 grams; 0.2 mole) was added dropwise with stirring while holding the temperature about 0° C. Triethylamine, 33.4 ml, was then added dropwise, with stirring, while keeping the temperature at about 5° to 10° C. The reaction mixture was stirred 16 hours at room temperature after the conclusion of the amine addition. The reaction mixture was then filtered, the solids washed with diethyl ether and the ether washings combined with the filtrate. The product O-(2-pyridyl) O-ethyl phosphorochloridothionate was left in solution for further reaction.

EXAMPLE 24

Preparation of O-(2-pyridyl) O-ethyl Phosphoramidothionate

The solution of O-(2-pyridyl) O-ethyl phosphorochloridothionate prepared in example 23 was charged into a glass reaction vessel fitted with a mechanical stirrer and thermometer. An additional 100 ml of ether was added and the solution cooled to 0° C. Ammonia gas was bubbled through the solution for one hour at 0° C., stirring was then continued for 16 hours at room temperature. The solution was then filtered, the solids obtained were washed with diethyl ether and these washings combined with the filtrate. The combined solution was washed twice with 50 ml of 0.1 N aqueous sodium hydroxide and four times with 50 ml portions of water. The solution was then dried and volatiles stripped off under reduced pressure to yield the desired product O-(2-pyridyl) O-ethyl phosphoramidothionate as a thick yellow liquid.

EXAMPLE 25

Preparation of O-(2-pyridyl) O-ethyl N-(dimethylaminomethylene) Phosphoramidothionate

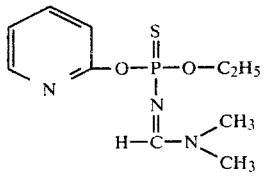

O-(2-Pyridyl) O-ethyl phosphoramidothionate (4.5 grams; 0.021 mole) and 50 ml of chloroform were charged into a glass reaction vessel fitted with a mechanical stirrer and thermometer. The dimethyl acetal of N,N-dimethylformamide (2.46 grams; 0.021 mole) was then added slowly with stirring at room temperature. The reaction mixture was held 48 hours. Solvent and unreacted reactants were then removed under reduced pressure, the residue was washed with hexane to remove hexane-soluble contaminants and the hexane stripped off under reduced pressure. The residue was dissolved in chloroform and the solution washed three times with water, dried, filtered and the solvent then removed under reduced pressure. The residue was placed under high vacuum for 1 hour to yield the desired product O-(2-pyridyl) O-ethyl N-(dimethylaminomethylene)phosphoramidothionate as a yellow liquid.

Additional compounds within the scope of this invention which can be prepared according to the procedures detailed in the foregoing example include:
O-(4-methyl-3-pyridyl) N-(1-aminopentylidene)-propylphosphonamidothionate, O-(4-ethyl-3-pyridyl) N-[(diethylamino)methylene)]butylphosphonamidothionate, O-(6-isopropyl-3-pyridyl) N-[1-(N'-ethylpropylamino)butylidene](1-ethylpropyl)phosphonamidothionate, O-(5-hexyl-2-pyridyl) N-[1-(N'-butyl-hexylamino)-3-methylpentylidene]phenylphosphonamidothionate, O-(4-hexyl-3-pyridyl) N-[(dimethylamino)hexylidene]-(5,5-dimethyl)hexylphosphonamidothionate, O-(5-methoxy-3-pyridyl), O-methyl N-[1-(dibutylamino)heptylidene]phosphoramidothionate, O-(4-ethoxy-3-pyridyl) O-butyl N-[(dimethylamino)phenylmethylene)]phosphoramidothionate, O-(5-methyl-4-pyridyl) O-propyl N-(1-aminopentylidene)phosphoramidothionate, O-(4-isopropyl-3-pyridyl) O-(1-ethylpropyl) N-[1-(diispropylamino)butylidene]phosphoramdiothionate, O-[5-(1-ethylbutyl)-2-pyridyl]O-isopropyl N-[(N'-ethyl-butylamino)methoxymethylene]phosphoramidothionate, O-(3-nitro-2-pyridyl) O-(5-methylpentyl) N-[(dibutylamino)-butoxymethylene]phosphoramidothionate, O-(5-nitro-2-pyridyl) S-ethyl N-[(dihexylamino)(3-methylpentyloxy)methylene)]phosphoramidothiolothionate, O-(4-fluoro-3-pyridyl) S-hexyl N-[(N'-methyl-propylamino)(methylthio)methylene]phosphoramidothiolothionate, O-(5-bromo-2-pyridyl) S-nonyl N-[(pentylamino)(2,2-dimethylethylthio)methylene]phosphoramidothiolothionate, O-(5,6-dibromo-2-pyridyl) S-isopropyl N-[(dimethylamino)(-propylthio)methylene]phosphoramidothiolothionate, O-(3-methyl-4-bromo-5-nitro-2-pyridyl) S-octyl N-(butoxymethylene)phosphoramidothiolate, O-(3,5,6-trichloro-4-pyridyl) N-[1-pentylamino)pentylidene)]-phenylphosponamidate, O-(4-methyl-5-chloro-6-bromo-2-pyridyl) S-propyl N-[(dipropylamino)Butoxymethylene]phosphoramidothiolate, O-(2-octyloxy-3,5-dichloro-4-pyridyl) S-(1,1-dimethylbutyl) N-[[N'-(1,1-dimethylethyl)-propylamino)](2,3-dimethylbutylthio)-methylene]]phosphoramidothiolothionate, O-(4,6-dibromo-3-pyridyl) N-[(N'-ethyl-pentylamino)methylene]ethylphosphonamidothionate, O-(4,5-dinitro-6-chloro-2-pyridyl) S-decyl N-(hexyloxymethylene)phosphoramidothiolate, O-(5-methyl-4-pyridyl) N-[(phenyl)(methoxy)methylene]ethylphosphonamidothionate, O-(3,5,6-trichloro-2-pyridyl) N-[(phenyl)(dipropylamino)methylene]propylphosphonamidothionate, O-(6-methyl-3-pyridyl) N-[1-(phenyl)hexylidene](2,2-dimethylhexyl)phosphonamidothionate, O-(6-methyl-3-pyridyl) N-[(phenyl)(propylthio)methylene]hexylphosphonamidate, O-(6-methyl-3-pyridyl) S-ethyl N-[(phenyl)(diethylamino)methylene]phosphoramidothiolothionate, O-(2-methyl-4-pyridyl) O-phenylmethyl N-(hexyloxymethylene)phosphoramidate, O-(3-methyl-4-pyridyl) O-(3,5-dibromophenyl-2-ethyl) N-[(pentylamino)(methylthio)methylene]phosphoramidothionate, O-(2,3-dibromo-5-pyridyl) S-phenyl N-[(N'-methyl-butylamino)methylene]phosphoramidothiolothionate.

For practical use as insecticides, the compounds of this invention are generally incorporated intp insecticidial compositions which comprise an inert carrier and an insecticidally toxic amount of such a compound. Such insecticidal compositions, which can also be called formulations, enable the active compound to be applied conveniently to the site of the insect infestation in any desired quantity. These compositions can be solids, such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of insecticides can be dispersed under superatomospheric pressure as aerosols. However, preferred liquid insecticidal compositions are emulsifiable concentrates, which comprise an active compound according to this invention and as the inerti carrier a solvent and an emulsifier. Such emulsifiable concentrates can be extended with water for application as sprays to the site of the insect infestation. The emulsifiers most commonly used in these concentrates are nonionic or mixtures of nonionic with anionic surface-active agents.

A typical insecticidal composition according to this invention is illustrated by the following example, in which the quantities are in parts by weight.

EXAMPLE 26

| PREPARATION OF A DUST | |
| --- | --- |
| Product of Example 3 | 10 |
| Powdered talc | 90 |

The above ingredients are mixed in a mechanical grinder-blender and are ground until a homogeneous, free-flowing dust of the desired particle size is obtained. This dust is suitable for direct application to the site of the insect infestation.

The compounds of this invention can be applied as insecticides in any manner recognized by the art. One method for detroying insects comprises applying to the locus of the insect infestation, an insecticidal composition comprising an inert carrier and, as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comrise from about 0.05 to about 95 percent by weight of the active compounds of this invention. In a preferred embodiment of this invention, the insecticidal compositions will comprise from about 5 to 75 percent by weight of the active compound. The compositions can also comprise such additional substances as other pesticides, stabilizers, spreaders, deactivators, adhesives, stickers, fertilizers, activators, synergists and the like.

The compounds of the present invention are also useful when combined with other insecticides in the insecticidal compositions heretofore described. These other insecticides can comprise from about 5 to about 95 percent of the active ingredients in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal composition to control insects, can include halogenated compounds such as DDT, methoxychlor, TDE, lindane, chlordane, isobenzan, aldrin, dieldrin, heptachlor, endrin, mirex, endosulfon, dicofol and the like; organic phoshporus compounds such as TEPP, schradan, ethion, parathion, PEN, demeton, carbophenothion phorate, zinophos, diazinon, malathion, mevinphcs, dimethoate, DBD, ronnel, oxydemeton-methyl, dicapthon, chlorothion, phosphamidon, naled, fenthion, trichlorofon, DDVP, and the like; organic nitrogen compound such as dinitro-o-cresol, dinitrocyclohexylphenol, DNB, DNP, binapacril, azobenzene and the like; organic carbamate compounds such as carbaryl, ortho 5353 and the like; organic sulphur compounds such as phenothiazine, phenoxathin, lauryl thiocyanate, [bis(2-thiocyanoethyl)ether], isobornyl thiocyanoacetate and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like.

The compounds of the present invention can also be combined with fungicidal and nematocidal chemical compounds to form pesticidal compositions useful for the control of fungi and in some cases soil nematodes as well as insects. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobenzenediazo sodium sulfonate and the like; while examples of nematocidal compounds are chloropicrin, O,O-diethyl O-(2,4-dichlorophenyl) phosphorothioate, tetrachlorothiophene, dazomet, dibromochloropropane and the like.

The new compounds of this invention can be used in many ways for the control of insects. Insecticides which are to be used as stomach poisons or protective materials can be applied to the surface on which the insects feed or travel. Insecticides which are to be used as contact posions or eradicants can be applied directly to the body of the insect, as a residual treatment to the surface on which the insect may walk or crawl, or as a fumigant treatmen of the air which the insect breathes. In some cases, the compounds applied to the soil or plant surfaces are taken up by the plant, and the insects are poisoned systematically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean bettle and the southern armyworm; the piercing-sucking insects, such as the pea aphid, the cereal leaf bettle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms or weevils, such as the codling moth, the alfalfa weevil, the cotton boll weevil, the pink boll worm, the plum curculio, the red banded leaf roller, the melonworm, the cabbage looper and the apple maggot, leaf miners such as the apple leaf miner, the birch leaf miner and the beet leaf miner, and gall insects such as the wheat joint worm and the grape phylloxera. Insects which attack below the surface of the ground are classified as subterranean insects and include such destructive pests as the wolly apple aphid, the Japanese beetle, the onion maggot and the corn rootworm.

The quantity of active compound of this invention to be used for insect control will depend on a variety of factors, such as the specific insect involved, intensity of the infestation, weather, type of environment, type of formulation and the like. For example, the application of only one or two ounces of active chemical per acre may be adequate for control of a light infestation of an insect under conditions unfavorable for its feeding while a pound or more of acive compound per acre may be required for the control of a heavy investation of insects under conditions favorable to their development.

The insecticidal activity of the compounds of the present invention was demonstrated by experiments carried out for the control of a variety of insects. In these experiments, the compounds to be tested are first put into a formulation suitable for application at various concentrations and application rates to plants and insects. The desired quantity of the test compound (the quantity being determined by the application concentration or application rate to be used in later testing) is dissolved or dispersed in a solvent consisting of acetone containing 3.19 grams/liter of Triton X ®-155 (alkylaryl polyether alcohol). When it has dissolved or dispersed in the acetone, 4 volumes of the acetone solution or dispersion are diluted with 96 volumes of distilled water. (If the test compound is insoluble in the acetone or distilled water it can be dispersed using a tissue grinder.) Lower concentration test solutions may be made by dilution of higher concentration solutions with a diluent consisting of 96 volumes distilled water and 4 volumes of acetone containing 3.19 grams of Triton X ®-155 per liter.

Test plants used in these experiments are prepared by planting the appropriate seeds in sterilized soil contained in plastic pots having an upper soil surface area of approximately 12.25 square inches (a square pot having a 3.5 inch side). After the seed has been planted, a layer of approximately 0.25 inches of sand is spread on the top surface of the soil. The test compound is applied after the plant has reached a specified size.

For foliar applications, the test compound, dissolved or dispersed in the water/acetone solvent described above, is sprayed as a mist onto the foliage of the test plants. The concentration of the test compound and the total quantity of solution applied is adjusted to give the application concentrations or rates desired. The plants are then allowed to air dry. Mites and aphids are exposed to treated leaves which have been left on the plant. Other insect species are exposed to treated leaves which have been removed from the plant and placed in petri dishes containing a piece of moist filter paper.

For soil drench applications, the test compound is first dissolved or dispersed in water/acetone as described above, then the amount of solution required to give a desired application rate is applied, using a pipette, evenly over the top of the soil in the pot. Twenty four hours after the treatment, mites and aphids are exposed to leaves which have been left on the treated plants. Other insect species are exposed to leaves which have been removed from the plants 24 hours after treatment and placed in petri dishes containing a piece of moist filter paper.

In direct contact applications, the test compound is, again, first formulated into a water/acetone solution, as described above, in the concentrations to be tested. Then the insect to be tested is dipped into, sprayed with or immersed in the liquid, dried, and observed for effect.

In the tables below setting forth the experimental data, PPM represents foliar application rates expressed as parts-per-million, #/A represents soil drench application rates expressed as pounds per acre.

CABBAGE LOOPER

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten cabbage loopers, second instar larval stage, are placed in each petri dish and the dish covered. Observations of insect mortality are made after 48 hours of exposure. Results of these tests are detailed in Table 1 below.

SOUTHERN ARMYWORM

Bush lima bean plants (Burpee Variety 222), two-leaf stage, are exposed, at various application rates, to the test compound applied both by the foliar spray and soil drench techniques. Leaves are removed from the plants—after approximately 30 minutes of air-drying for the foliar spray application, afer 24 hours for the soil drench application—and placed in petri dishes containing a piece of moist filter paper. Ten southern armyworms, second instar larval stage, are place in each petri, dish and the dish covered. Observations of insect mortality are made after 48 hours of exposure. Results of these tests are detailed in Table 2 below.

SOYBEAN LOOPER

Bush lima bean plants (Burpee Variety 222), two-leaf stage, are exposed, as various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten second instar larval soybean loopers are placed in each petri dish and the dish covered. Observations of insect mortality are made after 48 hours of exposure. Results of these tests are detailed in Table 3 below.

TOBACCO BUDWORM

Bush lima bean plants (Burpee Variety 222), two-leaf stage, are exposed, at various application rates, to the test compound applied both by the foliar spray ad soil drench techniques. Leaves are removed from the plants—after approximately 30 minutes of air-drying for the foliar spray application, after 24 hours for the soil drench application—and placed in petri dishes containing a piece of moist filter paper. Ten tobacco budworms, second instar larval stage, are placed in each petri dish and the dish covered. Observations of insect mortality are made after 48 hours of exposure. Results of these tests are detailed in Table 4 below.

MEXICAN BEAN BEETLE

Bush lima bean plants (Burpee Variety 222), two-leaf stage, are exposed, at various application rates, to the text compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten mexican bean bettles, second instar larval stage, are placed in each petri dish and the dish covered. Observations of insect mortality are made after 48 hours of exposure. Results of these tests are detailed in Table 5 below.

BOLL WEEVIL

Cotton plants (Deltapine 16), two leaf stage, are exposed, at various application rates, to the test compound applied both by the foliar spray and soil drench techniques. Leaves are removed from the plants—after approximately 30 minutes of air-drying for the foliar spray application, after 24 hours for the soil drench application—and placed in petri dishes containing a piece of moist filter paper. Ten adult boll weevils are placed in each petri dish and the dish is then covered. Observations of insect mortality are made after 48 hours of exposure. Results of these tests are detailed in Table 6 below.

GREEN PEACH APHID

Nasturtium plants (Burpee Mixed single Variety 4161) in the 2–3 leaf stage are treated with the test compound, at various application rates, both by the foliar spray and soil drench methods. The plants are air dried for about 30 minutes after the foliar spray is applied, then 25–50 green peach aphids are put on each treated plant and on an untreated control plant by placing an untreated leaf containing 25–50 adult and nymph green peach aphids on the plants. Twenty four hours after a plant has been treated by the soil drench method, it is infested by 24–50 aphids using the technique described above. An untreated control plant is similarly infested. After 48 hours of exposure of the insects to the treated plants, insect mortality is determined by comparison of the number of insects on the treated plants to the number on the untreated control plant. Results of this testing are set forth in Table 7 below.

PEA APHID

Pea plants (Burpee Wando) in the 10–14 day stage are treated with the test compound, at various application rares, both by the foliar spray and soil drench methods. The plants are air dried for about 30 minutes after the foliar spray is applied, then 25–50 pea aphids, adults and nymphs, are put on each treated plant and on an untreated control plant with a small paint brush. Twenty four hours after a plant has been treated by the soil drench method, it is infested by 25–50 aphids using the technique described above. An untreated control plant is similarly infested. After 48 hours of exposure of the insects to the treated plants, insect mortality is determined by comparison of the number of insects on the treated plants to the number on the untreated control plant. Results of this testing are set forth in Table 8 below.

TWO SPOTTED MITE

Bush lima bean plants (Burpee Variety 222) in the two-leaf stage are treated with the test compound, at various application rates, both by the foliar spray and soil drench methods. The plants are air dried for about 30 minutes after the foliar spray is applied, then 50–100 two spotted mites, adults and nymphs, are put on each treated plant and on an untreated control plant by placing an untreated infested bean leaf containing 50–100 mites on the plants. Twenty four hours after a plant has been treated by the soil drench method, it is infested by 50–100 mites using the technique described above. An untreated control plant is similarly infested. After 48 hours of exposure of the insects to the treated plants, insect mortality is determined by comparison of the number of insects on the treated plants to the number on the untreated control plant. Results of this testing are set forth in Table 9 below.

HOUSEFLY

Ten adult Houseflies are placed in a small (2"–3") wire screen cage fitted with a plastic cap. The cage is sprayed with the test compound at the desired concentrations in the form of a solution prepared as described hereinabove. After spraying, the treated cages are stored until dry. Sixty minutes after spraying, readings are made of knock down. The cages are then placed on paper toweling moistened with 5–10% sucrose solution and stored on this toweling for 23 hours at which time the 24 hours-after-treatment mortality reading is taken. The results of this test are given in Table 10 below.

GERMAN COCKROACH

Solutions of test compounds are formulated as described hereinbefore and the solution which gives a desired applicaation concentration is placed in a flask. Ten german cockroach adults are placed in a teaspoon tea strainer and are dipped into the test solution. The excess solution is shaken off, the tea strainer opened and the insects placed in a clear plastic container containing a small moist piece of dental wick. The container then is capped with a cover pierced with air holes. Insect mortality is observed 48 hours after the exposure. Results of this testing are indicated in Table 11 below.

SOUTHERN CORN ROOTWORM

A newly germinated corn seed is placed in a one ounce plastic cup fitted witl a snap-on plastic lid and covered with approximately 5 grams of sterilized soil. The test compound is formulated into solutions as described hereinbefore and applied to the soil as a soil drench at the desired application rates. After application, the lids are snapped on the cups and the cups are allowed to stand for about 15 minutes to permit the solution to spread evenly through tle soil. The lids are tlen removed, five second instar rootworm larvae are placed on the treated soil and tle cups recapped. The cup is examined for insects mortality after 72 hours of exposure. Larvae which cannot crawl or right themselves are considered dead. Results of this testing are given in Table 12 below.

YELLOW FEVER MOSQUITO

Solutions containing the test compound in the desired concentrations are formulated as described hereinabove. Each test solution is placed in a 10 ounce foamed polystyrene cup. Approximately ten 3–4 days old yellow fever mosquito larvae are placed in each test solution with an eyedropper. To each solution is then added a very small pinch of brewer's yeast and a very small piece of dry food (pulverized solid dog chow). Mortality data are taken after 48 hours of exposure. These data are shown in Table 13 below.

TABLE 1

| TEST COMPOUND | RATE PPM or #/A | PERCENT CONTROL | | | | | | | | | | |
|---|---|---|---|---|---|---|---|---|---|---|---|---|
| | | 1024 | 512 | 256 | 128 | 64 | 32 | 16 | 8 | 4 | 2 | 1 |
| Compound of Example 3 | PPM | 100 | 100 | 70 | 80 | 40 | — | — | — | — | — | — |
| | #/A | — | — | — | — | 20 | — | — | — | — | — | — |
| Compound of Example 6 | PPM | 100 | 90 | 60 | 60 | 50 | — | — | — | — | — | — |
| | #/A | — | — | — | — | 50 | — | — | — | — | — | — |
| Compound of Example 9 | PPM | — | 0* | 0* | 0* | 0* | — | — | — | — | — | — |
| | #/A | — | — | — | — | — | 13* | 13* | 3* | 0 | 10 | 10 |
| Compound of Example 10 | PPM | — | — | 30 | 10 | 0 | — | — | — | — | — | — |
| | #/A | — | — | — | — | — | 20 | 0 | 10 | — | — | — |
| Compound of Example 11 | PPM | — | — | 0 | 10 | 0 | — | — | — | — | — | — |
| | #/A | — | — | — | — | — | 0 | 0 | 0 | — | — | — |
| Compound of Example 14 | PPM | — | — | 100 | 50 | 20 | — | — | — | — | — | — |
| | #/A | — | — | — | — | — | 0 | 10 | 0 | — | — | — |
| Compound of Example 15 | PPM | — | — | 60 | 0 | 10 | — | — | — | — | — | — |
| | #/A | — | — | — | — | — | 0 | 0 | 0 | — | — | — |
| Compound of Example 16 | PPM | — | 50 | 10* | 10* | 0* | — | — | — | — | — | — |
| | #/A | — | — | — | — | — | 5* | 5* | 5* | 0 | 10 | 0 |
| Compound of Example 19 | PPM | — | — | 30 | 30 | 10 | — | — | — | — | — | — |
| | #/A | — | — | — | — | — | 10 | — | — | — | — | — |
| Compound of Example 22 | PPM | 60 | — | — | — | — | — | — | — | — | — | — |
| | #/A | — | — | — | — | 70 | — | — | — | — | — | — |
| Compound of Example 25 | PPM | — | — | 0 | — | — | — | — | — | — | — | — |
| | #/A | — | — | — | — | — | 0 | — | — | — | — | — |

*Values are average of two replicates
+ Values are average of three replicates

TABLE 2

| TEST COMPOUND | RATE PPM or #/A | PERCENT CONTROL | | | | | | | | | | |
|---|---|---|---|---|---|---|---|---|---|---|---|---|
| | | 1024 | 512 | 256 | 128 | 64 | 32 | 16 | 8 | 4 | 2 | 1 |
| Compound of Example 3 | PPM | 100 | 100 | 100 | 30 | 0 | — | — | — | — | — | — |
| | #/A | — | — | — | — | 10 | — | — | — | — | — | — |
| Compound of Example 6 | PPM | 100 | 100 | 90 | 40 | 20 | — | — | — | — | — | — |
| | #/A | — | — | — | — | 10 | — | — | — | — | — | — |
| Compound of Example 9 | PPM | — | 10 | 15* | 5* | 0* | — | — | — | — | — | — |
| | #/A | — | — | — | — | — | 3+ | 0+ | 3+ | 10 | 0 | 0 |
| Compound of Example 10 | PPM | — | — | 90 | 70 | 0 | — | — | — | — | — | — |
| | #/A | — | — | — | — | — | 0 | 0 | 0 | — | — | — |
| Compound of Example 11 | PPM | — | — | 30 | 20 | 10 | — | — | — | — | — | — |
| | #/A | — | — | — | — | — | 0 | 0 | 0 | — | — | — |
| Compound of Example 14 | PPM | — | — | 60 | 60 | 10 | — | — | — | — | — | — |
| | #/A | — | — | — | — | — | 0 | 10 | 0 | — | — | — |
| Compound of Example 15 | PPM | — | — | 100 | 50 | 70 | — | — | — | — | — | — |
| | #/A | — | — | — | — | — | 10 | 30 | 0 | — | — | — |
| Compound of Example 16 | PPM | — | 100 | 60* | 10* | 10* | — | — | — | — | — | — |
| | #/A | — | — | — | — | — | 10* | 5* | 20* | 0 | 10 | 0 |
| Compound of Example 19 | PPM | — | — | — | — | — | — | — | — | — | — | — |
| | #/A | — | — | — | — | — | 10 | — | — | — | — | — |
| Compound of Example 22 | PPM | 0 | — | — | — | — | — | — | — | — | — | — |
| | #/A | — | — | — | — | 100 | 0 | 0 | 0 | — | — | — |
| Compound of Example 25 | PPM | — | — | 10 | — | — | — | — | — | — | — | — |
| | #/A | — | — | — | — | — | 0 | — | — | — | — | — |

*Values are average of two replicates
+ Values are average of three replicates

TABLE 3

| TEST COMPOUND | RATE PPM or #/A | PERCENT CONTROL | | | | | | | | | | |
|---|---|---|---|---|---|---|---|---|---|---|---|---|
| | | 1024 | 512 | 256 | 128 | 64 | 32 | 16 | 8 | 4 | 2 | 1 |
| Compound of Example 9 | PPM | — | 0 | 0* | 5* | 0* | — | — | — | — | — | — |
| | #/A | — | — | — | — | — | 0+ | 6+ | 0+ | 10 | 20 | 0 |
| Compound of Example 10 | PPM | — | — | 0 | 0 | 0 | — | — | — | — | — | — |
| | #/A | — | — | — | — | — | 0 | 0 | 0 | — | — | — |
| Compound of Example 11 | PPM | — | — | 0 | 0 | 0 | — | — | — | — | — | — |
| | #/A | — | — | — | — | — | 0 | 0 | 0 | — | — | — |
| Compound of Example 14 | PPM | — | — | 10 | 0 | 0 | — | — | — | — | — | — |
| | #/A | — | — | — | — | — | 0 | 0 | 0 | — | — | — |
| Compound of Example 15 | PPM | — | — | 50 | 0 | 0 | — | — | — | — | — | — |
| | #/A | — | — | — | — | — | 0 | 0 | 10 | — | — | — |
| Compound of Example 16 | PPM | — | 30 | 20* | 0* | 0* | 0* | — | — | — | — | — |
| | #/A | — | — | — | — | — | 5* | 10* | 5* | 10 | 0 | 10 |
| Compound of Example 19 | PPM | — | — | 0 | 0 | 0 | — | — | — | — | — | — |
| | #/A | — | — | — | — | — | 0 | — | — | — | — | — |
| Compound of Example 22 | PPM | 50 | — | — | — | — | — | — | — | — | — | — |
| | #/A | — | — | — | — | 90 | 50 | — | — | — | — | — |
| Compound of Example 25 | PPM | — | — | 10 | — | — | — | — | — | — | — | — |

TABLE 3-continued

| TEST COMPOUND | RATE PPM or #/A | PERCENT CONTROL |||||||||||
|---|---|---|---|---|---|---|---|---|---|---|---|
| | | 1024 | 512 | 256 | 128 | 64 | 32 | 16 | 8 | 4 | 2 | 1 |
| | #/A | — | — | — | — | — | 0 | — | — | — | — | — |

*Values are average of two replicates
‡ Values are average of three replicates

TABLE 4

| TEST COMPOUND | RATE PPM or #/A | PERCENT CONTROL |||||||||||
|---|---|---|---|---|---|---|---|---|---|---|---|
| | | 1024 | 512 | 256 | 128 | 64 | 32 | 16 | 8 | 4 | 2 | 1 |
| Compound of Example 9 | PPM | — | — | 0 | 5* | 10* | — | — | — | — | — | — |
| | #/A | — | — | — | — | — | 0+ | 0+ | 0+ | 0 | 0 | 0 |
| Compound of Example 10 | PPM | — | — | 30 | 20 | 0 | — | — | — | — | — | — |
| | #/A | — | — | — | — | — | 10 | 0 | 10 | — | — | — |
| Compound of Example 11 | PPM | — | — | 20 | 0 | 0 | — | — | — | — | — | — |
| | #/A | — | — | — | — | — | 0 | 0 | 0 | — | — | — |
| Compound of Example 14 | PPM | — | — | 70 | 40 | 20 | — | — | — | — | — | — |
| | #/A | — | — | — | — | — | 0 | 0 | 10 | — | — | — |
| Compound of Example 15 | PPM | — | — | 100 | 0 | 40 | — | — | — | — | — | — |
| | #/A | — | — | — | — | — | 0 | 40 | 0 | — | — | — |
| Compound of Example 16 | PPM | — | — | 0 | 20* | 10* | — | — | — | — | — | — |
| | #/A | — | — | — | — | — | 0* | 0* | 0* | 0 | 0 | 0 |
| Compound of Example 19 | PPM | — | — | 60 | 40 | 10 | — | — | — | — | — | — |
| | #/A | — | — | — | — | — | 0 | — | — | — | — | — |
| Compound of Example 22 | PPM | 20 | — | — | — | — | — | — | — | — | — | — |
| | #/A | — | — | — | — | 90 | 40 | 20 | 0 | 0 | — | — |
| Compound of Example 25 | PPM | — | — | 30 | — | — | — | — | — | — | — | — |
| | #/A | — | — | — | — | — | 0 | — | — | — | — | — |

*Values are average of two replicates
‡ Values are average of three replicates

TABLE 5

| TEST COMPOUND | RATE PPM or #/A | PERCENT CONTROL |||||||||||
|---|---|---|---|---|---|---|---|---|---|---|---|
| | | 1024 | 512 | 256 | 128 | 64 | 32 | 16 | 8 | 4 | 2 | 1 |
| Compound of Example 3 | PPM | 100* | 100* | 100* | 100* | 95* | 80 | 80 | 70 | — | —5 | — |
| | #/A | — | — | — | — | 20 | — | — | — | — | — | — |
| Compound of Example 6 | PPM | 100 | 100 | 100 | 100 | 100 | — | — | — | — | — | — |
| | #/A | — | — | — | — | 20 | — | — | — | — | — | — |
| Compound of Example 9 | PPM | — | 90 | 15* | 10* | 5* | — | — | — | — | — | — |
| | #/A | — | — | — | — | — | 13+ | 3+ | 10+ | 10 | 10 | 20 |
| Compound of Example 10 | PPM | — | — | 100 | 90 | 10 | — | — | — | — | — | — |
| | #/A | — | — | — | — | — | 20 | 0 | 0 | — | — | — |
| Compound of Example 11 | PPM | — | — | 100 | 100 | 70 | — | — | — | — | — | — |
| | #/A | — | — | — | — | — | 80 | 70 | 0 | — | — | — |
| Compound of Example 14 | PPM | — | — | 100 | 80 | 90 | — | — | — | — | — | — |
| | #/A | — | — | — | — | — | 50 | 100 | 40 | — | — | — |
| Compound of Example 15 | PPM | — | — | 100 | 90 | 30 | — | — | — | — | — | — |
| | #/A | — | — | — | — | — | 80 | 50 | 0 | — | — | — |
| Compound of Example 16 | PPM | — | 100 | 100* | 95* | 100* | — | — | — | — | — | — |
| | #/A | — | — | — | — | — | 110* | 100* | 90* | 80 | 0 | 20 |
| Compound of Example 19 | PPM | — | — | 100 | 100 | 100 | — | — | — | — | — | — |
| | #/A | — | — | — | — | — | 100 | — | — | — | — | — |
| Compound of Example 22 | PPM | 100 | 100 | 100 | 100 | 100* | 100 | 100 | 90 | — | — | — |
| | #/A | — | — | — | — | 100 | 100 | 20 | 20 | — | — | — |
| Compound of Example 25 | PPM | — | — | 100 | — | — | — | — | — | — | — | — |
| | #/A | — | — | — | — | — | 100 | — | — | — | — | — |

*Values are average of two replicates
‡ Values are average of three replicates

TABLE 6

| TEST COMPOUND | RATE PPM or #/A | PERCENT CONTROL |||||||||||
|---|---|---|---|---|---|---|---|---|---|---|---|
| | | 1024 | 512 | 256 | 128 | 64 | 32 | 16 | 8 | 4 | 2 | 1 |
| Compound of Example 3 | PPM | 100 | 60 | 60 | 50 | — | — | — | — | — | — | — |
| | #/A | — | — | — | — | 20 | — | — | — | — | — | — |
| Compound of Example 6 | PPM | 40 | 50 | 20 | 30 | — | — | — | — | — | — | — |
| | #/A | — | — | — | — | 20 | — | — | — | — | — | — |
| Compound of Example 9 | PPM | — | 0 | 25* | 0 | 0 | — | — | — | — | — | — |
| | #/A | — | — | — | — | — | 10+ | 7+ | 7+ | 20 | 0 | 0 |
| Compound of Example 10 | PPM | — | — | 0 | 0 | 0 | — | — | — | — | — | — |
| | #/A | — | — | — | — | — | 10 | 0 | 0 | — | — | — |
| Compound of Example 11 | PPM | — | — | 60 | 30 | 10 | — | — | — | — | — | — |
| | #/A | — | — | — | — | — | 0 | 0 | 0 | — | — | — |
| Compound of Example 14 | PPM | — | — | 0 | 0 | 0 | — | — | — | — | — | — |
| | #/A | — | — | — | — | 0 | 0 | 0 | — | — | — | — |
| Compound of Example 15 | PPM | — | — | 60 | 10 | 10 | — | — | — | — | — | — |

TABLE 6-continued

| TEST COMPOUND | RATE PPM or #/A | PERCENT CONTROL | | | | | | | | | | |
|---|---|---|---|---|---|---|---|---|---|---|---|---|
| | | 1024 | 512 | 256 | 128 | 64 | 32 | 16 | 8 | 4 | 2 | 1 |
| | #/A | — | — | — | — | — | 30 | 30 | 20 | — | — | — |
| Compound of Example 16 | PPM | — | 30 | 55* | 50 | 30 | — | — | — | — | — | — |
| | #/A | — | — | — | — | — | 30* | 50* | 30* | 20 | 0 | 0 |
| Compound of Example 19 | PPM | — | — | — | — | — | — | — | — | — | — | — |
| | #/A | — | — | — | — | — | 50 | — | — | — | — | — |
| Compound of Example 22 | PPM | 100 | 80 | 20 | 0 | 0 | — | — | — | — | — | — |
| | #/A | — | — | — | — | 30 | — | — | — | — | — | — |
| Compound of Example 25 | PPM | — | — | 10 | — | — | — | — | — | — | — | — |
| | #/A | — | — | — | — | — | 50 | — | — | — | — | — |

*Values are average of two replicates
· Values are average of three replicates

TABLE 7

| TEST COMPOUND | RATE PPM or #/A | PERCENT CONTROL | | | | | | | | | | |
|---|---|---|---|---|---|---|---|---|---|---|---|---|
| | | 1024 | 512 | 256 | 128 | 64 | 32 | 16 | 8 | 4 | 2 | 1 |
| Compound of Example 3 | PPM | 100 | 92 | 90 | 60 | 75 | — | — | — | — | — | — |
| | #/A | — | — | — | — | 70 | — | — | — | — | — | — |
| Compound of Example 6 | PPM | 100 | 100 | 100 | 85 | 80 | — | — | — | — | — | — |
| | #/A | — | — | — | — | 70 | — | — | — | — | — | — |
| Compound of Example 9 | PPM | — | 100 | 60 | 50 | 10 | — | — | — | — | — | — |
| | #/A | — | — | — | — | — | 100* | 95* | 65* | 40 | 40 | 0 |
| Compound of Example 16 | PPM | — | 100 | 80 | 80 | 80 | — | — | — | — | — | — |
| | #/A | — | — | — | — | — | 100 | 100 | 100 | 100 | 80 | 50 |
| Compound of Example 22 | PPM | 100 | 95 | 90 | 85 | 80 | — | — | — | — | — | — |
| | #/A | — | — | — | — | 100 | 100 | 100 | 100 | 98 | 80 | 37 |

TABLE 8

| TEST COMPOUND | RATE PPM or #/A | PERCENT CONTROL | | | | | | | | | | | | |
|---|---|---|---|---|---|---|---|---|---|---|---|---|---|---|
| | | 1024 | 512 | 256 | 128 | 64 | 32 | 16 | 8 | 4 | 2 | 1 | 0.1 | 0.25 | 0.125 |
| Compound of Example 3 | PPM | 100 | 99 | 100 | 100 | 99 | 100* | 85 | 0 | — | — | — | — | — | — |
| | #/A | — | — | — | — | — | — | — | — | 100 | 100* | 100* | 85* | 30 | 0 |
| Compound of Example 6 | PPM | 100 | 100 | 100 | 100 | 100 | 100 | 100 | 88 | — | — | — | — | — | — |
| | #/A | — | — | — | — | — | — | — | — | — | — | — | — | — | — |
| Compound of Example 9 | PPM | — | 100 | 50 | 0 | 0 | — | — | — | — | — | — | — | — | — |
| | #/A | — | — | — | — | — | 45* | 20* | 0* | 0 | 0 | — | — | — | — |
| Compound of Example 16 | PPM | — | 100 | 100 | 100 | 100 | — | — | — | — | — | — | — | — | — |
| | #/A | — | — | — | — | — | 100 | 100 | 100 | 100 | 100 | 100 | — | — | — |
| Compound of Example 19 | PPM | — | — | 100 | 100 | 100 | — | — | — | — | — | — | — | — | — |
| | #/A | — | — | — | — | — | 100 | — | — | — | — | — | — | — | — |
| Compound of Example 22 | PPM | 100 | 100 | 100 | 100 | 98* | 92 | 90 | 50 | — | — | — | — | — | — |
| | #/A | — | — | — | — | 100 | 100 | 100 | 100 | 100 | 100 | 100* | 100 | 0 | — |
| Compound of Example 25 | PPM | — | — | 100 | — | — | — | — | — | — | — | — | — | — | — |
| | #/A | — | — | — | — | — | 100 | — | — | — | — | — | — | — | — |

*Values are average of two replicates

TABLE 9

| TEST COMPOUND | RATE: PPM or #/A | PERCENT CONTROL | | | | | | | | | | |
|---|---|---|---|---|---|---|---|---|---|---|---|---|
| | | 1024 | 512 | 256 | 128 | 64 | 32 | 16 | 8 | 4 | 2 | 1 |
| Compound of Example 3 | PPM | 94 | 97 | 96 | 93 | 90 | — | — | — | — | — | — |
| | #/A | — | — | — | — | 60 | — | — | — | — | — | — |
| Compound of Example 6 | PPM | 95 | 95 | 94 | 92 | 70 | — | — | — | — | — | — |
| | #/A | — | — | — | — | 80 | — | — | — | — | — | — |
| Compound of Example 9 | PPM | — | 20 | 40* | 10* | 0* | — | — | — | — | — | — |
| | #/A | — | — | — | — | — | 35+ | 43+ | 13+ | 0 | 0 | 0 |
| Compound of Example 10 | PPM | — | — | 50 | 20 | 10 | — | — | — | — | — | — |
| | #/A | — | — | — | — | — | 50 | 20 | 20 | — | — | — |
| Compound of Example 11 | PPM | — | — | 80 | 50 | 30 | — | — | — | — | — | — |
| | #/A | — | — | — | — | — | 100 | 100 | 100 | — | — | — |
| Compound of Example 14 | PPM | — | — | 80 | 80 | 60 | — | — | — | — | — | — |
| | #/A | — | — | — | — | — | 90 | 80 | 50 | — | — | — |
| Compound of Example 15 | PPM | — | — | 100 | 95 | 80 | — | — | — | — | — | — |
| | #/A | — | — | — | — | — | 100 | 100 | 90 | — | — | — |
| Compound of Example 16 | PPM | — | 100 | 100* | 97* | 95* | — | — | — | — | — | — |
| | #/A | — | — | — | — | — | 100* | 100* | 99* | 96 | 94 | 80 |
| Compound of Example 19 | PPM | — | — | 100 | 100 | 90 | — | — | — | — | — | — |
| | #/A | — | — | — | — | — | 90 | — | — | — | — | — |
| Compound of Example 22 | PPM | 100 | 100 | 98 | 100 | 92* | 50 | 30 | 10 | — | — | — |
| | #/A | — | — | — | — | 100 | 100 | 98 | 90 | 80 | 20 | 0 |
| Compound of Example 25 | PPM | — | — | 0 | — | — | — | — | — | — | — | — |

TABLE 9-continued

| TEST COMPOUND | RATE: PPM or #/A | PERCENT CONTROL | | | | | | | | | |
|---|---|---|---|---|---|---|---|---|---|---|---|
| | | 1024 | 512 | 256 | 128 | 64 | 32 | 16 | 8 | 4 | 2 | 1 |
| | #/A | — | — | — | — | — | 0 | — | — | — | — | — |

*Values are average of two replicates
† Values are average of three replicates

TABLE 10

| TEST COMPOUND | RATE (PPM) | PERCENT CONTROL | | | | | | | |
|---|---|---|---|---|---|---|---|---|---|
| | | 1024 | 512 | 256 | 128 | 64 | 32 | 16 | 8 |
| Product of Example 3 | k | 70 | 50 | 40 | 10 | 20 | 30 | 10 | 0 |
| | m | 100 | 100 | 100 | 100 | 100 | 70 | 40 | 0 |
| Product of Example 6 | k | 100 | 100 | 30 | 40 | 0 | 20 | 30 | 20 |
| | m | 100 | 100 | 100 | 100 | 90 | 90 | 50 | 20 |
| Product of Example 9 | k | — | 100 | 90* | 70* | 100* | — | — | — |
| | m | — | 100 | 100* | 100* | 55* | — | — | — |
| Product of Example 10 | k | — | — | 100 | 100 | 90 | — | — | — |
| | m | — | — | 100 | 100 | 60 | — | — | — |
| Product of Example 11 | k | — | — | 30 | 40 | 100 | — | — | — |
| | m | — | — | 100 | 80 | 100 | — | — | — |
| Product of Example 14 | k | — | — | 100 | 100 | 100 | — | — | — |
| | m | — | — | 100 | 100 | 100 | — | — | — |
| Product of Example 15 | k | — | — | 100 | 100 | 90 | — | — | — |
| | m | — | — | 100 | 100 | 100 | — | — | — |
| Product of Example 16 | k | — | 100 | 90* | 50* | 50* | — | — | — |
| | m | — | 100 | 100* | 100* | 80* | — | — | — |
| Product of Example 19 | K | — | — | 30 | 0 | 0 | — | — | — |
| | m | — | — | 50 | 0 | 0 | — | — | — |
| Product of Example 22 | k | 100 | 100 | 100 | 70 | 95* | 100 | 100 | 100 |
| | m | 100 | 100 | 100 | 90 | 95* | 90 | 90 | 80 |
| Product of Example 25 | k | — | — | 40 | — | — | — | — | — |
| | m | — | — | 90 | — | — | — | — | — | k = 60 minute knockdown
m = 24 hour mortality
* = values are available of two replicates

TABLE 11

| TEST COMPOUND | RATE (PPM) | PERCENT CONTROL | | | | | | | |
|---|---|---|---|---|---|---|---|---|---|
| | | 1024 | 512 | 256 | 128 | 64 | 32 | 16 | 8 |
| Compound of Example 3 | | 100 | 100 | 100 | 20 | 100 | 85* | 80 | 20 |
| Compound of Example 9 | | — | 70 | 45* | 40* | 5* | — | — | — |
| Compound of Example 10 | | — | — | 100 | 90 | 50 | — | — | — |
| Compound of Example 11 | | — | — | 20 | 60 | 10 | — | — | — |
| Compound of Example 14 | | — | — | 100 | 100 | 70 | — | — | — |
| Compound of Example 15 | | — | — | 100 | 100 | 100 | 10 | 0 | 0 |
| Compound of Example 16 | | — | 60* | 60* | 15* | 0* | 0 | 0 | 0 |
| Compound of Example 19 | | — | — | 0 | 0 | 0 | — | — | — |
| Compound of Example 22 | | 90 | 30 | 10 | 0 | 0 | — | — | — |
| Compound of Example 25 | | — | — | 0 | — | — | — | — | — |

*Values are average of two replicates

TABLE 12

| TEST COMPOUND | RATE (#/A) | PERCENT CONTROL | | | | | | | |
|---|---|---|---|---|---|---|---|---|---|
| | | 64 | 32 | 16 | 8 | 4 | 2 | 1 | 0.5 | 0.25 |
| Compound of Example 3 | | — | — | 100(a) | 100(a) | 100(a) | 100(a) | 80(a) | — | — |
| Compound of Example 6 | | — | — | 100(a) | 100(a) | 60(a) | 60(a) | 40(a) | — | — |
| Compound of Example 9 | | 100 | — | 100 | — | — | — | 20 | 50 | 20 |
| Compound of Example 10 | | — | — | 100 | 100 | 90 | 90 | 30 | 50 | 30 |
| Compound of Example 11 | | — | — | 80 | — | — | — | — | — | — |
| Compound of Example 14 | | — | — | 100 | 100 | 100 | 100 | 50 | 80 | 60 |
| Compound of Example 15 | | — | — | — | — | — | — | 70 | 60 | 50 |
| Compound of Example 16 | | 100 | — | 100(1) | 100 | 95(3) | 86(2) | 83(2) | 80(2) | 100(1) |
| Compound of Example 19 | | — | — | — | — | 90 | 100 | 80 | 30 | — |
| Compound of Example 22 | | 100 | 100 | 100 | 100(1) | 100(1) | 100(1) | 90(1) | — | — |
| Compound of Example 25 | | — | — | 30 | — | — | — | — | — | — |

(a)48 Hour Mortality
(1)Values are average of two replicates
(2)Values are average of three replicates
(3)Values are average of four replicates

TABLE 13 hz,1/32

| TEST COMPOUND | (PPM) | PERCENT CONTROL | | | |
|---|---|---|---|---|---|
| | | 10.0 | 1.0 | 0.1 | 0.01 |
| Compound of Example 3 | | 100 | 100 | 100 | 100 |
| Compound of Example 6 | | 100 | 100 | 100 | 100 |
| Compound of Example 9 | | 100 | 100 | 50 | 40 |
| Compound of Example 10 | | 100 | 100 | 80 | 30 |
| Compound of Example 11 | | 100 | 100 | 80 | 80 |
| Compound of Example 14 | | 100 | 100 | 90 | 50 |
| Compound of Example 15 | | 100 | 100 | 40 | 70 |
| Compound of Example 16 | | 100 | 100 | 100 | 40 |
| Compound of Example 19 | | 100 | 100 | 100 | 80 |
| Compound of Example 22 | | 100 | 100 | 100 | 50 |

I claim:

1. A compound of the formula

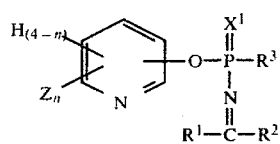

wherein $X^1$ is selected from the group consisting of oxygen and sulfur; $R^1$ is selected from the group consisting of hydrogen, alkyl, phenyl lower alkoxy and lower alkylthio; $R^2$ is selected from the group consisting of, amino, lower alkylamino and di lower alkylamino; Z is selected from the group consisting of lower alkyl, lower alkoxy, nitro and halogen; and n is an integer from 0 to 4; and wherein $R^3$ is selected from the group consisting of lower alkyl, lower alkoxy, lower alkylthio and

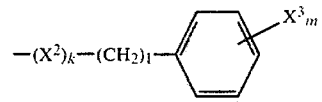

wherein $X^2$ is selected from the group consisting of oxygen and sulfur; $X^3$ is halogen; K is the integer 0 or 1; and l and m are each integers from 0 to 3.

2. The compound of claim 1, O-(3,5,6-trichloro-2-pyridyl) O-ethyl N-(dimethylaminomethylene)phosphoramidothionate.

3. The compound of claim 1, O-(3,5,6-trichloro-2-pyridyl) N-(dimethylaminomethylene)ethylphosphonamidothionate.

4. The compound of claim 1, O-(2-chloro-3-pyridyl) O-ethyl N-(dimethylaminomethylene)phosphoramidothionate.

5. The compound of claim 1, O-(6-methyl-3-pyridyl) O-ethyl N-(dimethylaminomethylene)phosphoramidothionate.

6. The compound of claim 1, O-(3-pyridyl) O-ethyl N-(dimethylaminomethylene)phosphoramidothionate.

7. The compound of claim 1, O-(3-pyridyl) N-(dimethylaminomethylene)ethylphosphonamidothionate.

8. The compound of claim 1, O-(2-pyridyl) O-ethyl N-(dimethylaminomethylene)phosphoramidothionate.

9. An insecticidal composition comprising an inert carrier and, as an essential active ingredient, in an effective amount, a compound of claim 1.

10. A method of controlling insects which comprises contacting said insects with an insecticidal composition comprising an inert carrier and, as an essential active ingredient, in an effective amount, a compound of claim 1.

* * * * *